United States Patent
Blass

(10) Patent No.: US 6,635,769 B1
(45) Date of Patent: Oct. 21, 2003

(54) PROCESS FOR MAKING FUNCTIONALIZED OXAZOLIDINONE COMPOUNDS

(75) Inventor: Benjamin Eric Blass, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/009,081

(22) PCT Filed: May 16, 2000

(86) PCT No.: PCT/US00/13435

§ 371 (c)(1), (2), (4) Date: Nov. 8, 2001

(87) PCT Pub. No.: WO00/69837

PCT Pub. Date: Nov. 23, 2000

Related U.S. Application Data

(60) Provisional application No. 60/134,821, filed on May 19, 1999.

(51) Int. Cl.[7] ..................... C07D 263/20; C07D 263/22
(52) U.S. Cl. .................................................... 548/229
(58) Field of Search .......................................... 548/229

(56) References Cited

FOREIGN PATENT DOCUMENTS

| JP | 02-049725 A | 2/1990 |
|---|---|---|
| WO | WO 99/37630 A1 | 7/1999 |

OTHER PUBLICATIONS

Duc et al., Synthese Organique–N–alkylation de l'oxazolidone–2 sur supports solides mineraux, C. R. acad. Sc. Paris, 300(16), pp. 799–802, (1985).*

Poindexter, G. S. et al., "The Use of 2–Oxazolidinones as Latent Aziridine Equivalents. 2. Aminoethylation of Aromatic Amines, Phenols, and Thiophenols", *J. Org. Chem.*, 1992, pp. 6257–6265, vol. 57.

Botella, J. M. et al., "Aminolyse de Carbamates Cycliques analogues de la Carboxybiotine; Catalyse Metallique et Modelisation de Transfert de Carboxyle", *Tetrahedron*, 1992, pp. 5111–5122, vol. 48, No. 24. Abstract Only.

Herweh, J. E. et al., "N–p–Toluenesulfonyl–2–oxazolidones Via the Cycloaddition Reaction of p–Toluenesulfonyl Isocyanate and Epoxides", *J. of Heterocyclic Chem.*, 1971, pp. 983–987, vol. 8, No. 6.

Yamawaki, J. et al., "N–Alkylation of Amides and N–heterocycles with Potassium Fluoride on Alumina", *Chemistry Letters*, 1981, pp. 1143–1146, No. 8.

Buchstaller, H–P, "Solid Phase Synthesis of Oxazolidinones via a Novel Cyclisation/Cleavage Reaction", *Tetrahedron*, 1998, pp. 3465–3470, vol. 54, No. 14.

Hole, P. T. et al., "Solid–Phase Synthesis of 3,5–Disubstituted 1,3–Oxazolidin–2–ones by an Activation/Cyclo–elimination Process", *Tetrahedron*, 1998, vol. 39, No. 40.

Blass, B. E. et al., "A Facile KF/AL$_2$O$_3$ Mediated Method for the Synthesis of Substituted Oxazolidinones", *Tetrahedron Letters*, 1999, pp. 6545–6547, vol. 40, No. 36.

* cited by examiner

*Primary Examiner*—Joseph K. McKane
*Assistant Examiner*—Rebecca Anderson
(74) *Attorney, Agent, or Firm*—Richard S. Echler, Sr.; Milton B. Graff

(57) ABSTRACT

The subject invention involves process for making fuctionalized oxazolidinones having structure (1) wherein: (a) R1 and R2 are each independently selected from hydrogen, alkyl, aryl and heterocycle, or R1 and R2 are attached to form a cycloalkyl, aryl or heterocyclic ring; (b) R3 is selected from primary and secondary alkly (—R6), —SO$_2$—R4, and —C(O)NH—R5; (c) R4 is aryl; and (d) R5 is alkyl or aryl; the process comprising a reaction step carried out in a reaction mixture, wherein an oxazolidinone is reacted with an electrophile selected from R6-Br, R6-I, R4-SO$_2$Cl, and R5-NCO; the reaction mixture comprising a non-protic and non-oxidizing solvent and potassium fluoride on alumina; and without the presence of a substantial amount of a strong base in the reaction mixture. The subject invention also involves libraries of functionalized oxazolidinone compounds and their preparation using such processes.

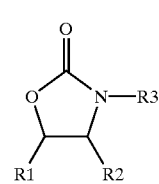

(1)

5 Claims, No Drawings

PROCESS FOR MAKING FUNCTIONALIZED OXAZOLIDINONE COMPOUNDS

This application is a 371 of PCT/US00/13435 filed May 16, 2000, which claims benefit of Ser. No. 60/134,821 filed May 19, 1999.

FIELD OF THE INVENTION

The subject invention relates to processes for making certain functionalized oxazolidinone compounds.

SUMMARY OF THE INVENTION

The subject invention involves processes for making compounds having the structure:

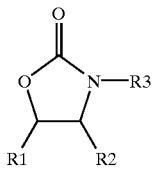

wherein:
(a) R1 and R2 are each independently selected from hydrogen, alkyl, aryl and heterocycle, or R1 and R2 are attached to form a cycloalkyl, aryl or heterocyclic ring;
(b) R3 is selected from primary and secondary alkyl (—R6), —SO$_2$—R4, and —C(O)NH—R5;
(c) R4 is aryl; and
(d) R5 is alkyl or aryl;
the process comprising a reaction step carried out in a reaction mixture, wherein an oxazolidinone having the structure:

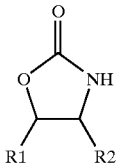

is reacted with an electrophile selected from R6-Br, R6-I, R4-SO$_2$Cl, and R5-NCO; the reaction mixture comprising a non-protic and non-oxidizing solvent and potassium fluoride on alumina; and without the presence of a substantial amount of a strong base in the reaction mixture.

DESCRIPTION OF THE INVENTION

Glossary of Terms

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkylacyl). Preferred linear alkyl have from one to about twenty carbon atoms, more preferably still from one to about ten carbon atoms, more preferably still from one to about six carbon atoms, still more preferably from one to about four carbon atoms; most preferred are methyl or ethyl. Preferred cyclic and branched alkyl have from three to about twenty carbon atoms, more preferably from three to about ten carbon atoms, more preferably still from three to about seven carbon atoms, still more preferably from three to about five carbon atoms. Preferred cyclic alkyl have one hydrocarbon ring, but may have two, three, or more, fused or spirocycle hydrocarbon rings. Preferred alkyl are unsaturated with from one to about three double or triple bonds, preferably double bonds; more preferably they are mono-unsaturated with one double bond. Still more preferred alkyl are saturated. Saturated alkyl are referred to herein as "alkanyl". Alkyl unsaturated only with one or more double bonds (no triple bonds) are referred to herein as "alkenyl". Alkyl unsaturated with one or more triple bonds are referred to herein as "alkynyl". Preferred substituents of alkyl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, sulfo, alkylsulfo, arylsulfo, sulfino, alkylsulfino, arylsulfino, phospho, alkylphospho, arylphospho, phosphino, alkylphosphino, arylphosphino, nitro, and cyano. Substituents of cycloalkyl also include cycloalkyl, aryl and heterocyclic rings which are fused or spirocycle with the initial cycloalkyl. Also, unsubstituted alkyl are preferred. An alkyl is bonded to another moiety at the "attaching carbon" of the alkyl. As used herein, "primary alkyl" means that the attaching carbon of the alkyl has two or three hydrogens bonded to it; "secondary alkyl" means that the attaching carbon has one hydrogen bonded to it; and "tertiary alkyl" means that the attaching carbon has no hydrogens bonded to it.

As used herein, "heteroatom" means a nitrogen, oxygen, or sulfur atom.

As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryl have from six to about fourteen, preferably to about ten, carbon atoms in the aromatic ring(s), and a total of from about six to about twenty, preferably to about twelve, carbon atoms. Preferred aryl is phenyl or naphthyl; most preferred is phenyl (Ph). Preferred substituents of aryl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, sulfo, alkylsulfo, arylsulfo, sulfino, alkylsulfino, arylsulfino, phospho, alkylphospho, arylphospho, phosphino, alkylphosphino, arylphosphino, nitro, and cyano. Substituents of aryl also include cycloalkyl and heterocyclic rings which are fused with the aryl ring or rings. Also, unsubstituted aryl are preferred.

As used herein unless specified otherwise, "heterocycle" or "heterocyclic" means a saturated, unsaturated or aromatic cyclic hydrocarbon ring (or fused rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the rings(s); and a total of from three to about twenty carbon plus heteroatoms, more preferably from three to about ten, more preferably still five or six, carbon plus heteroatoms. Preferred heterocycles have one ring, but may have two, three, or more, fused rings. More preferred heterocyclic rings include those which are one ring with 5 or 6 carbon plus heteroatoms in the ring with no more than three ring heteroatoms, no more than two of which are O and S. Still more preferred are such 5- or 6-ring atom heterocycles with one or two ring atoms being O or S and the others being C; or with one, two or three ring atoms being N and the others being C. Such preferred 5- or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-ring atom heterocyclic ring. Heterocycles are unsubstituted or substituted. Preferred heterocycle substituents are the same as for alkyl.

As used herein, "strong base" means an inorganic hydroxide base, alkyl-alkali metal (e.g., n-butyllithium), alkali metal hydride (e.g., sodium hydride), alkoxide salt (e.g., sodium methoxide), alkali metal amide (e.g., lithium diisopropyl amide), and the like.

As used herein, "substantial amount" means a sufficient amount of a specified material such that it effects a subject invention process in a measurable way.

As used herein, "non-protic and non-oxidizing solvent" means a solvent that does not dissociate to provide a substantial and measureable proton concentration, and does not have substantial oxidizing potential. Protic solvents include, for example, water, methanol, ethanol, dimethylformamide and the like. Oxidizing solvents include, for example, dimethylsulfoxide, and the like.

As used herein "combinatorial library" of compounds means a mixture of related compounds or a group of individual compounds, e.g. in separate wells of a reaction block, made substantially simultaneously by substantially the same process using a mixture of or individual related reactants to obtain related compounds.

Processes of the Invention

The subject invention processes involve the use of a solid supported reagent for the preparation of functionalized oxazolidinones, either individually or in libraries. As a class, oxazolidinones have been shown to possess a wide range of biological activity, including antidepressant, antihistaminic, antiftingal, antihypertensive, and antibacterial activity. A brief examination of the literature reveals that most common methods for the preparation of functionalized oxazolidinones require the use of strong bases (i.e. n-BuLi, NaH, etc.) and an aqueous work-up. The preparation of combinatorial libraries of oxazolidinones is greatly simplified by the subject processes which preferably avoid both of these steps. The functionalization of oxazolidinones in the 2-position is accomplished using potassium fluoride on alumina (KF/Al$_2$O$_3$) as a base in the presence of a suitable electrophile.

In addition to the preparation of single compounds, the subject invention processes are useful for the preparation of combinatorial libraries through the use of a reagent on solid support (KF on alumina). This approach, which sits between conventional solution phase chemistry and resin bound techniques, shares several advantages of both fields. As with solid phase synthesis, excess support bound reagent can be used to drive reactions to completion and then be removed by filtration, avoiding cumbersome work-ups. Unlike resin based chemistry, however, the target compound is not covalently bound to the solid support, so monitoring of the reactions and analysis can be accomplished using standard methods (thin layer chromatography, solution $^1$H NMR, etc.). Finally, the products are isolated by filtration and removal of the solvents, eliminating the need for the cleavage step required in solid phase preparations.

Processes of the subject invention involve preparation of functionalized oxazolidinones having the structure:

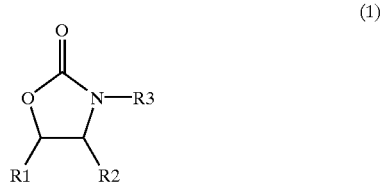

(1)

In structure (1), R1 and R2 are each independently selected from hydrogen, alkyl, aryl, and heterocycle, or R1 and R2 are attached (R1/R2) forming a cycloalkyl, aryl, or heterocyclic ring. Preferred R1 and R2 are independently selected from hydrogen, alkyl, and aryl. Preferred alkyl R1 and R2, and non-aromatic rings that are R1 or R2 or R1/R2, are unsubstituted or substituted, preferably with: fluoro, chloro, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfmo, alkylsulfino, arylsulfino, phospho, alkylphospho, arylphospho, phosphino, alkylphosphino, arylphosphino, nitro and cyano; more preferably with: alkyl, aryl, alkoxy, aryloxy, alkylthio, arylthio, alkyl and aryl esters. Preferred aryl and aromatic heterocycle R1, R2 and R1/R2 are unsubstituted or substituted, preferably with: halo, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfmo, alkysulfino, arylsulfino, phospho, alkylphospho, arylphospho, phosphino, alkylphophino, arylphosphino, nitro, and cyano; more preferably with: halo, alkyl, alkoxy, aryloxy, alkylthio, arylthio, alkyl and aryl esters, and nitro.

In structure (1), R3 is selected from primary and secondary alkyl (R6), SO$_2$-R4, and —C(O)NH—R5. R4 is aryl. R5 is alkyl or aryl.

R6 is a primary or secondary alkyl, preferably having from 1 to about 12 carbon atoms, more preferably from 1 to about 8 carbon atoms, more preferably still from I to about 4 carbon atoms. Such alkyl R6 is unsubstituted or substituted, such substituents preferably being selected from fluoro, chloro, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, arylsulfino, phospho, alkylphospho, arylphospho, phosphino, alkylphosphino, arylphosphino, nitro and cyano; more preferably from alkyl, aryl, alkoxy, aryloxy, alkylthio, arylthio, alkyl and aryl esters, alkylphospho, arylphospho, and cyano.

R4 is aryl, preferably phenyl. Such aryl R4 is unsubstituted or substituted, such substituents preferably being selected from halo, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, arylsulfino, phospho, alkylphospho, arylphospho, phosphino, alkylphosphino, arylphosphino, nitro, and cyano; more preferably from halo, alkyl, alkoxy, aryloxy, alkylthio, arylthio, alkyl and aryl esters, alkylacyl, and arylacyl.

When R5 is alkyl, it is a primary, secondary or tertiary alkyl, preferably having from 1 to about 12 carbon atoms, more preferably from 1 to about 8 carbon atoms, more preferaly still from 1 to about 4 carbon atoms. Such alkyl. R5 is unsubstituted or substituted, such substituents preferably being selected from halo, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, arylsulfino, phospho, alkylphospho, arylphospho, phosphino, alkylphosphino, arylphosphino, nitro, and cyano; more preferably from alkyl, aryl, alkoxy, aryloxy, alkylthio, arylthio, alkyl and aryl esters.

When R5 aryl, the aryl is preferably phenyl. Such aryl R5 is unsubstituted or substituted, such substituents preferably being selected from halo, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, arylsulfino, phospho, alkylphospho, arylphospho, phosphino, alkylphosphino, arylphosphino, nitro, and cyano; such substituents preferably being selected from halo, alkyl, alkoxy, aryloxy, alkylthio, arylthio, alkyl and aryl esters, and nitro.

The processes of the subject invention comprise a reaction step wherein an oxazolidinone having the structure:

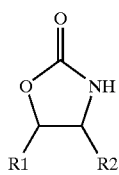

(2)

is reacted with an electrophile selected from R6-Br, R6-I, R4-SO$_2$Cl, and R5-NCO. R1, R2, R4, R5 and R6 are as defined hereinabove.

The above reaction step is carried out in a reaction mixture comprising solvent which non-protic and non-oxidizing. Preferred solvents are selected from dichloromethane, dichloroethane, chloroform, ethyl acetate, 1,4-dioxane, tetrahydrofuran, dimethoxyethane, and acetonitrile. When the electrophile R6-Br or R6-I is a reactant, more preferred solvents are selected from acetonitrile, 1,4-dioxane, tetrahydrofuran, dimethoxyethane, and ethyl acetate. When the electrophile R4-SO$_2$Cl is a reactant, more preferred solvents are dichloromethane and dichloroethane. When the reactant R5-NCO is used, more preferred solvents are selected from dichloromethane, chloroform, ethyl acetate, and 1,4-dioxane.

The reaction mixture comprises potassium fluoride on alumina. Potassium fluoride on alumina (KF/Al$_2$O$_3$) is typically from about 10% to about 60% KF, preferably about 40% KF. The amount of KF/Al$_2$O$_3$ present during the reaction step is preferably from about 6 equivalents to about 15 equivalents per equivalent of compound (2), more preferably from about 10 equivalents to about 12 equivalents per equivalent of compound (2).

In the above reaction step, the amount of electrophile reacted with compound (2) is typically from about 0.9 equivalent to about 1.5 equivalents, more preferably about 1.0 equivalents.

The above reaction step is preferably carried out at a temperature of from about 0° C. to about 95° C., more preferably at a temperature of from about 20° C. to about 80° C., more preferably still at about room temperature (about 25° C.). The above reaction step is preferably carried out for a period of from about 5 h to about 72 h, more preferably from about 10 h to about 36 h, more preferably still for about 24 h.

The above reaction step is preferably carried out without the presence of any substantial amount of a strong base in the reaction mixture, preferably less than about 0.15 equivalent strong base, more preferably less than about 0.01 equivalent, still more preferably with no strong base in the reaction mixture.

EXAMPLES

The following examples provide further information regarding the subject invention processes. They are simply exemplary and do not limit the scope of the subject invention.

Example 1

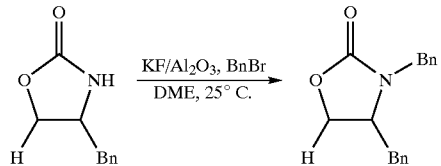

Alkylation of an oxazolidinone: 150 mg (0.85 mmol) of 4-benzyl-2-oxazolidinone and 1.5 g of KF/Al$_2$O$_3$ (40% by weight) are dissolved/suspended in 15.0 ml of dimethoxyethane (DME) and 145 mg (101 ul, 0.85 mmol) of benzyl (Bn) bromide is added. The reaction is then stirred vigorously at room temperature for 24 hours, filtered, and stripped of solvent to yield the product.

Example 2

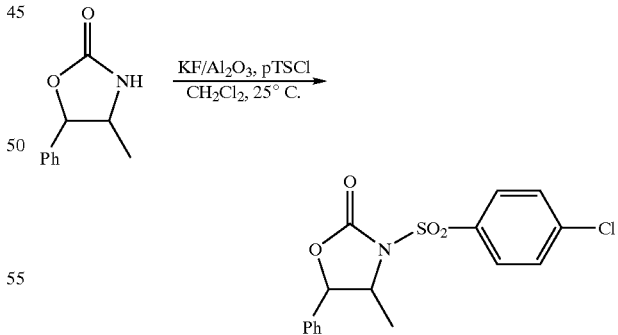

Sulfonylation of an oxazolidinone: 150 mg (0.85 mmol) of 4-methyl-5-phenyl-2-oxazolidinone and 1.5 g of KF/Al$_2$O$_3$ (40% by weight) are dissolved/suspended in 15.0 ml of dichloromethane and 161.4 mg (0.85 mmol) of p-tolylsulfonyl chloride (pTSCl) is added. The reaction is then stirred vigorously at room temperature for 24 hours, filtered, and stripped of solvent to yield the product.

Example 3

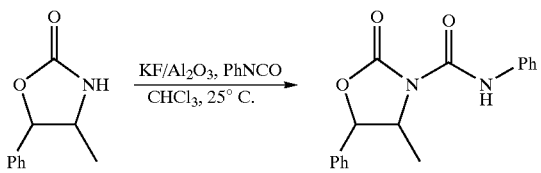

Condensation of an oxazolidinone with an isocyanate: 150 mg (0.85 mmol) of 4-methyl-5-phenyl-2-oxazolidinone and 1.5 g of KF/Al$_2$O$_3$ (40% by weight) are dissolved/suspended in 15.0 ml of chloroform and 101 mg (92 ul, 0.85 mmol) of phenyl isocyanate (PhNCO) is added. The reaction is then stirred vigorously at room temperature for 24 hours, filtered, and stripped of solvent to yield the product.

Example 4

Alkylation Library: Four oxazolidinones are dissolved in DME to a concentration of 0.6M and then mixed in equal portions so as to create a solution that is 0.6M in overall concentration of oxazolidinone, but 0.15M for each individual oxazolidinone. This solution is then distributed to 32 vials containing 258 mg of KF/Al$_2$O$_3$ (40% by weight) and diluted with 2.16 ml DME. 0.56 ml of an a solution of an alkyl halide (0.3M in DME) is added to each vessel using a total of 32 different alkyl halides. The reactions are then sealed and heated to 75–80° C. with vigorous stirring. After 24 hours, the reactions are cooled, filtered into 32 vials, and stripped of solvent to yield an oil (4 alkylated oxazolidinones per vial).

Example 5

Sulfonylation Library: A Robbin's reaction block with the bottom sealed is loaded with 100 mg of KF/Al$_2$O$_3$ per well. Eight oxazolidinones and twelve sulfonyl chlorides are then dissolved in dichloroethane at 0.1M and 0.15M, respectively. Each of the oxazolidinones is then distributed down one row of the plate (rows A–H), with 0.57 ml added per well. The sulfonyl chlorides are then distributed down each column (column 1–12), one sulfonyl chloride per column, 0.38 ml per well. The reaction block is then sealed and shaken for 24 hours at room temperature. The solution are then filtered into 96 vials and stripped of solvent to yield the library of products.

Example 6

Urea Library: A Robbin's reaction block with the bottom sealed is loaded with 100 mg of KF/Al$_2$O$_3$ per well. Eight oxazolidinones and twelve isocyantes are then dissolved in a 1:1 mixture of CHCl$_3$:EtOAc at 0.1M and 0.15M respectively. Each of the oxazolidinones is then distributed down one row of the plate (rows A–H), with 0.57 ml added per well. The isocyanates are distributed down each column (column 1–12), one isocyanate per column, 0.38 ml per well. The reaction block is sealed, shaken for 24 hours at room temperature, and then an additional 0.15 ml of 1:1 CHCl$_3$:EtOAc is added followed by 10 mg of a polyamine scavenger resin (4.53 mmol/g, tris(2-aminoethyl)amine, polymer blend, Aldrich Product No. 47210-7). The reaction block is resealed, shaken for 24 hours at room temperature, and then the solution are filtered into 96 vials and stripped of solvent to yield the library of products.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A process for making functionalized oxazolidinones having the structure:

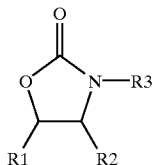

wherein:
(a) R1 is selected from the group consisting of hydrogen, alkyl, and aryl;
(b) R2 is alkyl substituted with aryl;
(c) R3 is R6 when R6 is selected from the group consisting of primary and secondary alkyl;
(d) R4 is aryl; and
(e) R5 is alkyl or aryl;

the process comprising a reaction step carried out in a reaction mixture, wherein an oxazolidinone having the structure:

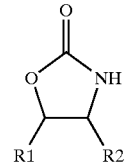

is reacted with an electrophile selected from the group consisting of R6-Br and R6-I; the reaction mixture comprising a non-protic and non-oxidizing solvent and potassium fluoride on alumina; and without the presence of a substantial amount of a strong base in the reaction mixture.

2. The process of claim 1 wherein:
(a) R1 is selected from the group consisting of hydrogen, alkyl having from 1 to about 12 carbon atoms, and aryl having from 6 to about 14 carbon atoms in the ring(s) being unsubstituted or substituted, such substituents being selected from the group consisting of fluoro, chloro, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, arylsulfino, phospho, alkylphospho, arylphospho, phosphino, alkylphosphino, arylphosphino, nitro, and cyano; any aromatic R1, being unsubstituted or substituted, such substituents being selected from the group consisting of halo, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, arylsulfino, phospho, alkylphospho, arylphospho, phosphino, alkylphosphino, arylphosphino, nitro, and cyano;
(b) R2 is alkyl substituted with aryl;
(c) R6 is a primary or secondary alkyl having from 1 to about 12 carbon atoms; R6 being unsubstituted or substituted, such substituents being selected from the group consisting of fluoro, chloro, alkyl, aryl, heterocycle, alkoxy, aryloxy, alkylthio, arylthio, formyl, alkylacyl, arylacyl, alkyl and aryl esters, sulfo, alkylsulfo, aryisulfo, sulfino, alkylsulfino, aryisulfino, phospho, alkylphospho, arylphospho, phosphino, alkylphosphino, arylphosphino, nitro, and cyano;

(d) R4 is aryl having from 6 to about 14 carbon atoms in the ring(s); R4 being unsubstituted or substituted, such substituents being selected from the group consisting of halo, alkyl, aryl, heterocycle, alkoxy, aryloxy, alkylthio, arylthio, formyl, alkylacyl, arylacyl, alkyl and aryl esters, sulfo, alkylsulfo, arylsulfo, sulfino, alkylsulfino, aryisulfino, phospho, alkylphospho, arylphospho, phosphino, alkylphosphino, arylphosphino, nitro, and cyano; and (e) R5 is alkyl having from 1 to about 12 carbon atoms or aryl having from 6 to about 14 carbon atoms; alkyl R5 being unsubstituted or substituted, such substituents being selected from the group consisting of halo, alkyl. aryl, heterocycle. alkoxy. aryloxy, alkylthio, arylthio, formyl, alkylacyl, arylacyl, alkyl and aryl esters, sulfo. alkylsulfo, aryisulfo, sulfino, alkylsulfino, arylsulfino, phospho. alkylphospho, arylphospho, phosphino, alkylphosphino, arylphosphino, nitro, and cyano; aryl R5 being unsubstituted or substituted, such substituents being selected from the group consisting of halo, alkyl, aryl, heterocycle, alkoxy. aryloxy, alkylthio, arylthio, formyl, alkylacyl, arylacyl, alkyl and aryl esters. sulfo, alkylsulfo, aryisulfo, sulfino, alkylsulfino, arylsulfino, phospho, alkylphospho, arylphospho, phosphino, alkylphosphino, arylphosphino, nitro, and cyano.

3. The process of claim 2 wherein:

(a) the reaction step is carried out in a solvent selected from the group consisting of dichloromethane, dichloroethane, chloroform, ethyl acetate, 1,4-dioxane, tetrahydrofuran, dimethoxyethane, and acetonitrile;

(b) the amount of potassium fluoride on alumina present during the reaction step is from about 6 equivalents to about 15 equivalents per equivalent of the oxazolidanone;

(c) the reaction step is carried out at a temperature of from about 0° C. to about 95° C. for a period of from about 5 h to about 72 h; and (d) the amount of strong base in the reaction mixture is less than about 0.15 equivalent per equivalent of oxazolidinone.

4. The process of claim 1 characterized in that the reaction step is carried out at room temperature for 24 h.

5. The process of claim 1 characterized in that all aryl are phenyl and the amount of strong base in the reaction mixture is less than 0.01 equivalent per equivalent of the oxazolidinone.

* * * * *

UNITED STATES PATENT AND TRADEMARK OFFICE
CERTIFICATE OF CORRECTION

PATENT NO.     : 6,635,769 B1
DATED          : October 21, 2003
INVENTOR(S)    : Benjamin Eric Blass It is certified that error appears in the above-identified patent and that said Letters Patent is hereby corrected as shown below:

Column 4,
Line 34, delete "sulfmo" and insert -- sulfino --.

Column 8,
Line 4, after "ring(s) and before being unsubstituted or substituted," please insert the missing portion -- ; any non-aromatic R1 --.

Signed and Sealed this

Seventeenth Day of August, 2004

JON W. DUDAS
*Acting Director of the United States Patent and Trademark Office*